(12) United States Patent
Ruhge et al.

(10) Patent No.: US 8,440,974 B2
(45) Date of Patent: May 14, 2013

(54) SYSTEM AND METHOD FOR ANALYSIS OF ULTRASONIC POWER COUPLING DURING ACOUSTIC THERMOGRAPHY

(75) Inventors: Forrest R. Ruhge, Orlando, FL (US); Clifford Hatcher, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 836 days.

(21) Appl. No.: 12/560,543

(22) Filed: Sep. 16, 2009

(65) Prior Publication Data
US 2011/0062339 A1   Mar. 17, 2011

(51) Int. Cl.
*G01J 5/00*   (2006.01)
*G01M 7/00*   (2006.01)
*G01N 29/46*   (2006.01)
*G01N 29/00*   (2006.01)

(52) U.S. Cl.
USPC ............ 250/342; 250/341.6; 250/358.1; 250/341.1; 73/588; 73/595; 73/584; 73/602

(58) Field of Classification Search ............ 73/632, 73/643, 1.82, 588, 582, 595, 600, 648, 649, 73/659, 643.1, 584, 602, 606; 708/403, 404, 708/300; 374/45, 121; 250/341.6, 342, 341.1, 250/334, 330, 358.1; 702/35; 348/163, 164
See application file for complete search history.

(56) References Cited

U.S. PATENT DOCUMENTS

| | | | |
|---|---|---|---|
| 5,111,046 | A | 5/1992 | Bantel |
| 6,690,016 | B1 | 2/2004 | Watkins et al. |
| 6,696,692 | B1 | 2/2004 | Pepper |
| 6,838,670 | B2 | 1/2005 | Lewis et al. |
| 2004/0051035 | A1 | 3/2004 | Zombo et al. |
| 2004/0089812 | A1 | 5/2004 | Favro et al. |
| 2005/0151083 | A1* | 7/2005 | Favro et al. ............ 250/341.6 |
| 2005/0167596 | A1 | 8/2005 | Rothenfusser et al. |
| 2007/0045544 | A1 | 3/2007 | Favro et al. |
| 2007/0288177 | A1 | 12/2007 | Rothenfusser et al. |
| 2008/0105055 | A1 | 5/2008 | Ringermacher et al. |

* cited by examiner

*Primary Examiner* — David Porta
*Assistant Examiner* — Yara Green

(57) ABSTRACT

A system and method of performing acoustic thermography in which invalid data is filtered from data used to detect defects on a structure. An ultrasonic sound input signal is provided to a structure to produce a thermal image output. A sensor senses an input energy corresponding to the sound input signal and produces an input energy signal. The input energy signal is transformed to a test spectrum and is compared to a reference spectrum. The comparison of the test spectrum to the reference spectrum is used to determine whether to include the thermal image output in an analysis for detecting defects in the structure.

19 Claims, 7 Drawing Sheets

SYSTEM AND METHOD FOR ANALYSIS OF ULTRASONIC POWER COUPLING DURING ACOUSTIC THERMOGRAPHY

FIELD OF THE INVENTION

The present invention relates generally to a system and method for detecting defects in a structure and, more particularly, to a system and method of performing acoustic thermography in which invalid data is filtered from data used to detect defects on a structure.

BACKGROUND OF THE INVENTION

Maintaining the structural integrity of certain structures is important in many fields because of safety concerns, downtime, cost, etc. Loss of structural integrity may be caused by material defects, such as cracks, delaminations, disbonds, corrosion, inclusions, voids, etc., that may exist in the structure. For example, it is important in the power generation industry that reliable techniques are available to examine the structural integrity of turbine, generator and associated balance of plant equipment to ensure the components and systems do not suffer failure during operation. A common method for detection of a crack or defect is visual examination by skilled personnel. However, it is known that cracks or defects that may affect the integrity of structural components may not be readily visible without the use of special techniques to aid the examiner. Therefore, various techniques have been developed in the art for the non-invasive and non-destructive analysis of different structural components and materials.

One known technique for the non-invasive and non-destructive analysis of a material for defects comprises thermal imaging where heat is generated in the material and is emitted as radiation in the infrared wavelengths. The location of certain types of defects may be identified as surface temperature variations, where the area of a defect has a temperature differential relative the surrounding area of the material. One implementation of thermal imaging comprises acoustic thermal imaging in which an ultrasonic excitation is used to generate heat in the material. In acoustic thermal imaging, an acoustic thermal effect occurs when sound waves propagate through a solid body or component that contains a crack or other defect causing it to vibrate. Because the faces of the crack ordinarily do not vibrate in unison as the sound waves pass, dissipative phenomena, such as friction between the faces, will convert some of the vibrational energy to heat. By combining this heating effect with infrared imaging, an efficient, non-destructive crack detection system can be realized.

The amount of energy transferred into the material for acoustic thermal imaging may vary, depending on the location and effectiveness of a coupling between an ultrasonic energy and a component being inspected as well as other factors and operating parameters. The amount of energy transferred into a component for acoustic thermal imaging may affect the validity, consistency and/or accuracy of the inspection process for individual components, and in a comparison of plural similar components.

SUMMARY OF THE INVENTION

In accordance with one aspect of the invention, a method of performing acoustic thermography on a structure is provided. The method comprises: applying a sound input signal to the structure; sensing an input energy corresponding to the sound input signal applied to the structure, and the sensing an input energy comprising producing an input energy signal corresponding to the sensed input energy; detecting a thermal release from the structure produced as a result of the sound input signal and producing an output signal effective to indicate a defect in the structure; verifying an input power of the sound input signal to the structure based on a comparison of the input energy signal to a reference signal; and performing a filtering of the output signal including identifying the output signal for inclusion in an analysis based on a comparison of the input energy signal to the reference signal.

The sensing an input energy may comprise receiving a vibration output from the structure at a sensor producing the input energy signal.

A Fourier transform may be applied to the input energy signal to provide a Fourier transform spectrum of the vibration output, and the reference signal may comprise a predetermined Fourier transform spectrum for comparison to the Fourier transform spectrum of the vibration output.

The Fourier transform spectrum of the vibration output and the predetermined Fourier transform spectrum each comprise peaks corresponding to harmonic response frequencies and the filtering may comprise identifying the output signal for inclusion in an analysis of the structure if the frequencies of a predetermined number of peaks in the Fourier transform spectrum of the vibration output occur at the same frequencies as the peaks in the predetermined Fourier transform spectrum.

The filtering may comprise identifying the output signal for inclusion in an analysis of the structure if the amplitude of the peaks in the Fourier transform spectrum of the vibration output substantially matches the amplitude of the peaks in the predetermined Fourier transform spectrum at predetermined corresponding frequencies.

The filtering may comprise implementing a correlation function to compare the Fourier transform spectrum of the vibration output to the predetermined Fourier transform spectrum and identifying the output signal for inclusion in an analysis of the structure if a correlation score of the correlation function is equal to or greater than a predetermined threshold value.

The sensing an input energy may comprise detecting an emitted sound signal emitted from the structure, and the emitted sound signal may be received by a microphone spaced from the structure and producing the input energy signal. Further, the sound input signal may comprise an ultrasonic sound input signal.

The detecting a thermal release may comprise receiving the thermal release at an infrared camera and producing the output signal.

In accordance with another aspect of the invention, a method of performing acoustic thermography on a structure is provided. The method comprises: applying an ultrasonic sound input signal to the structure; sensing an input energy corresponding to the sound input signal applied to the structure, and the sensing an input energy comprising receiving a vibration output from the structure at a sensor producing an input energy signal corresponding to the sensed input energy; applying a Fourier transform to the input energy signal to provide a Fourier transform spectrum of the vibration output; detecting a thermal release from the structure produced as a result of the sound input signal and producing an output signal effective to indicate a defect in the structure; verifying an input power of the sound input signal to the structure based on a comparison of the Fourier transform spectrum of the vibration output to a predetermined Fourier transform spectrum; and performing a filtering of the output signal including identifying the output signal for inclusion in an analysis of the structure if the input power of the sound input signal meets a predetermined criteria based on the comparison of the Fourier transform spectrum of the vibration output to the predetermined Fourier transform spectrum.

In accordance with a further aspect of the invention, a system is provided for performing acoustic thermography on a structure. The system comprises an acoustic energy source for applying a sound input signal to the structure and a sensor for sensing an input energy corresponding to the acoustic input signal applied from the acoustic energy source to the structure. The sensor produces an input energy signal corresponding to the sensed input energy. An infrared camera is configured to detect a thermal release from the structure produced as a result of the sound input signal and an output signal is produced indicative of a defect in the structure. A processor is provided for receiving the input energy signal and the output signal wherein the processor processes the input energy signal and verifies an input power of the sound input signal to the structure based on a comparison of the input energy signal to a reference signal. The processor performs a filtering of the output signal including identifying whether to include the output signal in an analysis of the structure based on the comparison of the input energy signal to the reference signal.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
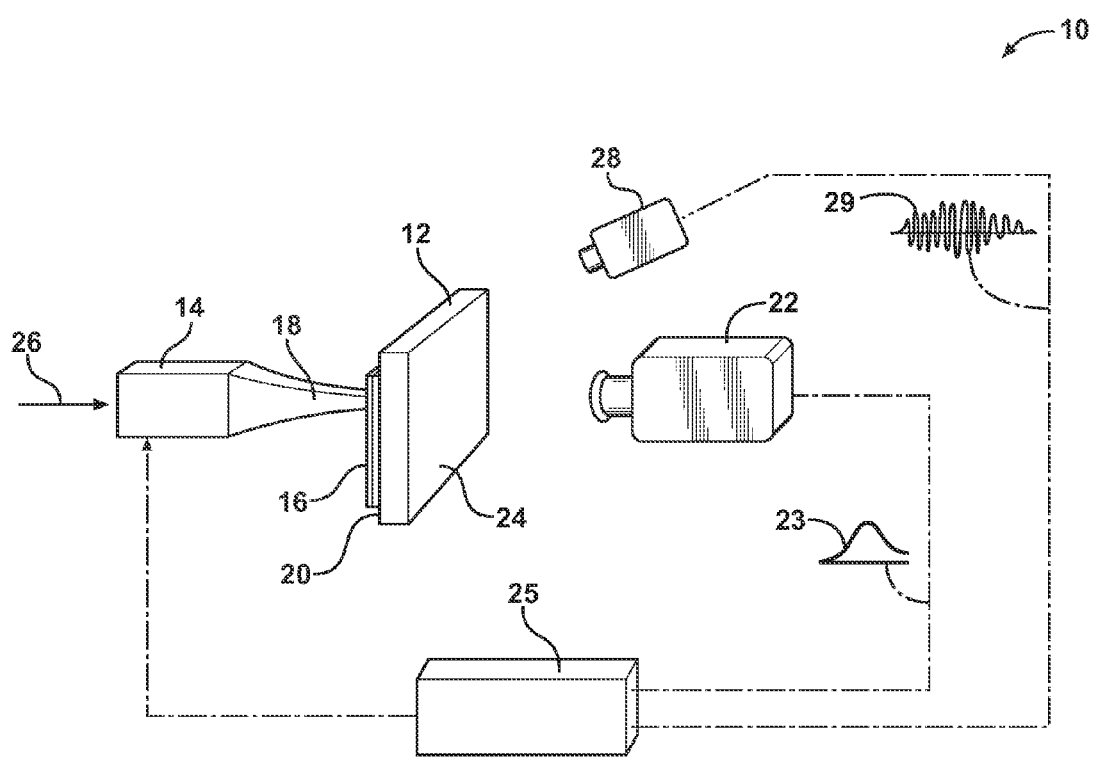
FIG. 1 is a block diagram of a defect detection system according to an embodiment of the invention.

FIG. 1 is a diagrammatic illustration of a defect detection system 10, according to an embodiment of the present invention. The system 10 may be used to detect defects, such as cracks, corrosion, delaminations, disbonds, etc., in a component 12. The component 12 is intended to represent any structural component or material, such as, e.g., a turbine blade, a turbine rotor, an aircraft skin, etc., that may include these types of defects. Although the component 12 being examined may typically comprise a structure formed of a metal alloy, the component 12 need not be metal, but can be other materials, such as ceramics, composites, etc.

The illustrated system 10 includes an acoustic energy source such as an ultrasonic transducer 14 that generates a sound input signal at a predetermined ultrasonic frequency or within a certain ultrasonic frequency band. The ultrasonic transducer 14 may include a horn 18 that couples the sound input signal into the component 12. The transducer 14 can be a conventional transducer suitable for the purposes of the thermosonic process of the present invention. The transducer 14 provides a transformation of electrical pulses into mechanical displacement by use of a piezoelectric element. For example, the transducer 14 may employ a PZT stack of piezoelectric crystals that are cut to precise dimensions and operate at a very narrow frequency as dictated by the cut dimension of the crystals. The PZT stack is mechanically coupled to the horn 18, and the tip of the horn 18 is pressed against the component 12. Because the tip has a fixed dimension and is inflexible, it exhibits a wide contact area and pressure within the area of contact. This is further influenced by a non-flat, non-smooth surface of the component 12. The transducer 14 can also be any other suitable sound device capable of generating heat in defects within the component 12, and may comprise a test fixture having a transducer for coupling to the component 12. In one embodiment, the transducer 14 generates pulses of ultrasonic energy at a frequency of about 20 kHz for a period of time of about one-half to one second. However, as will be appreciated by those skilled in the art, other ultrasonic or sonic frequencies, and pulse durations can be used within the scope of the present invention.

The ultrasonic energy from the transducer 14 may be coupled into the component 12 through a mechanical coupler 16. The coupler 16 is shown in mechanical contact with the transducer horn 18 and a front side 20 of the component 12. In one embodiment, the coupler 16 may be a non-linear coupler, such as an automotive gasket material, leather, duct tape, cork, TEFLON, paper, etc., that may help to transmit acoustic energy from the transducer 14 to the component 12. In other embodiments, the coupler 16 may be a thin piece of a soft metal, such as copper, to effectively couple the ultrasonic energy into the component 12. It is noted, however, that the transducer 14 may not require the coupler 16 to transmit an effective level of ultrasonic energy to the component 12. A force 26 is applied to the transducer 14 by any suitable device (not shown) to push the horn 18 against the coupler 16 and the component 12 or, alternatively, to push the horn 18 directly into engagement with the component 12. The amount of the force 26 applied to the transducer 14 is selected to provide an effective transmission of acoustic energy to the component 12.

The detection system 10 includes a thermal imaging camera 22 spaced a predetermined distance from the component 12, as shown. The camera 22 generates images of the component 12, represented as an output signal 23 of a thermal release, in conjunction with the ultrasonic excitation of the component 12. The camera 22 can be spaced from a back side 24 of the component 12 at any distance that is suitable to provide images of as much of the component 12 as desired in a single image to simultaneously detect multiple defects with the desired resolution. In other embodiments, the ultrasonic energy from the transducer 14 and the image generated by the camera 22 can be provided at the same side of the component 12 or any side of the component 12. The thermal camera 22 can be any camera suitable for the purposes described herein.

A sensor 28 is located near the component 12 to detect a vibration output from the component 12 as a result of the ultrasonic sound input from the ultrasonic transducer 14. In an embodiment of the invention, the sensor 28 comprises a microphone located in spaced relation adjacent to the component for receiving and sensing a vibration output and producing an input energy signal 29 corresponding to an input energy provided to the component 12 from the transducer 14.

According to the invention, acoustic energy is transmitted from the ultrasonic transducer 14 to the component 12, operating to effect an increase in the amount of thermal energy, and produce a corresponding thermal emission, at the defect in the component 12. In order to transmit an effective amount of acoustic energy to the component 12 to produce a thermal emission indicative of a defect, a correct combination of the force 26 applied to the transducer 14 and coupling to the component, i.e., coupling as may be provided through the material and thickness of the coupler 16, and frequency and duration of the sound input signal must be provided.

The system further includes a processor 25 for controlling a testing process for detecting defects in the component 12. The processor 25 may provide control signals to the transducer 14 for providing an ultrasonic sound input signal to the component 12. The processor 25 additionally receives the input energy signal 29 from the sensor 28 and the output signal 23 from the camera 22, and performs processing and filtering operations for analysis of the component 12, as is described further below.

Due to variations in the force 26 and other operational parameters in applying acoustic energy to the component 12, prior known operations have often relied on subjective or qualitative criteria, such as an audible analysis by skilled personnel to determine if proper conditions are present to provide sufficient input energy to obtain a valid output for detecting defects in the component 12. For example, in prior thermal imaging operations it has been observed that an acceptable image quality may be obtained from the camera 22 if an acoustic sound, or "horn screech" is sensed. It has been observed that the consistency of the defect detection process may vary depending on the personnel performing the inspection. Further, an improper analysis may occur if the thermography test does not produce a recognizable thermal emission due to insufficient energy being transmitted to the component 12 via the input sound signal from the transducer 14, and if such a condition is not properly identified by personnel performing the inspection.

In accordance with the present invention, an acoustic thermography analysis is provided for determining the existence of defects in the component 12 wherein an initial quantitative determination is made to evaluate the input ultrasonic energy for generating a detectable thermal output from the component 12. The initial quantitative determination provides an evaluation of the input acoustic energy to ensure that sufficient acoustic energy is input to the component 12 and to ensure that a consistent energy input between different evaluations is provided, as is described further below.

As described above, a sensor 28 comprising a microphone may be provided for sensing an input energy corresponding to a coupling conveying the sound input signal to the component 12. Specifically, the sensor 28 detects a vibration output from the component 12, which vibration output provides a measurable indication of whether predetermined criteria is met for producing a valid thermal image from defects in the component 12. It should be noted that the sensor 28 may comprise a single microphone or plural microphones located around the component 12. Further, the sensor 28 may comprise other vibration sensing devices for detecting a vibration output corresponding to the input energy provided to the component 12.

Figure 2:
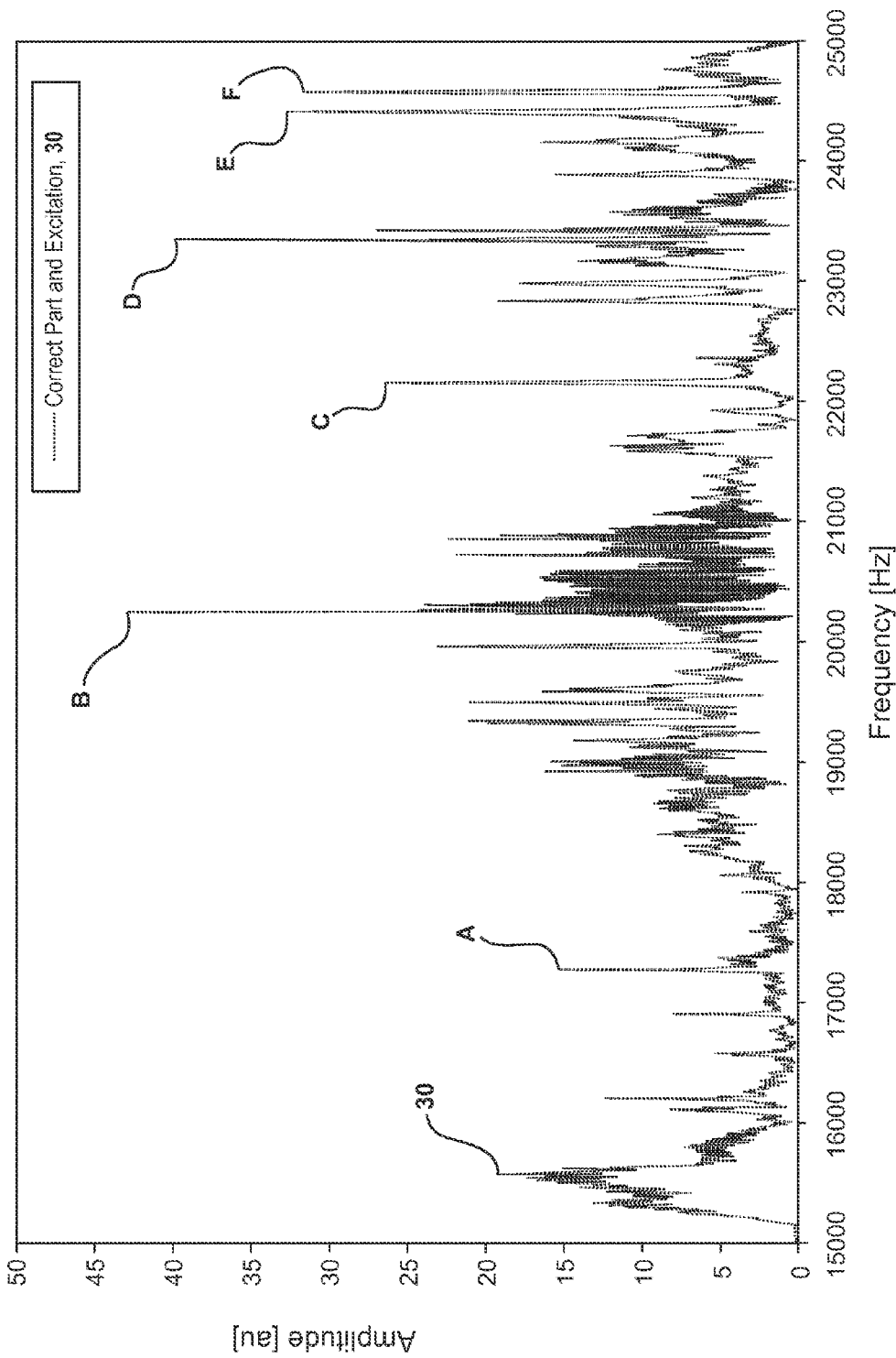
FIG. 2 shows a test spectrum comprising a Fourier transform spectrum of a sensed vibrational output from a component subjected to an applied sound input signal.
Figure 3:
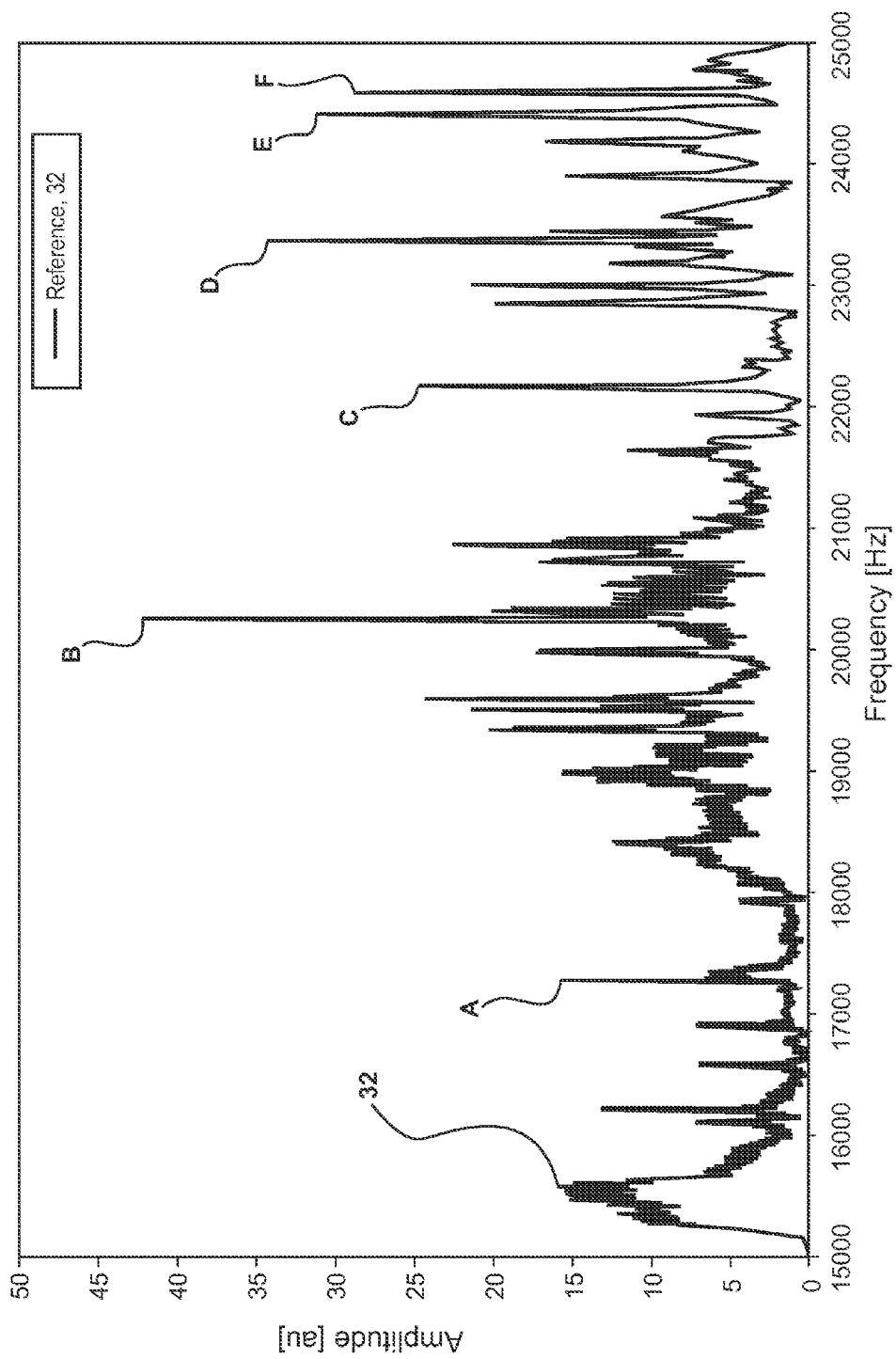
FIG. 3 shows a Fourier transform spectrum comprising a reference spectrum for comparison to the test spectrum for the component.

In a particular implementation of the invention, a Fourier transform is applied to the input energy signal 29 produced at the sensor 28 to convert the input energy signal 29 to the frequency domain and provide a Fourier transform spectrum of the vibration output. An example of a Fourier transform spectrum of a vibration output for a valid thermal imaging operation (test spectrum 30) is illustrated in FIG. 2, where the parameters controlling the input energy signal 29, i.e., the excitation energy, are correct for producing a thermal emission indicative of a defect in the component 12. The test spectrum 30 is compared to a predetermined or reference Fourier transform spectrum (reference spectrum 32) corresponding to a known desired or acceptable vibration output for the component 12, as seen in FIG. 3. The reference spectrum 32 may be created based on a known valid test for a component corresponding to the component 12 being evaluated. Alternatively, the reference spectrum 32 may be created using vibration output data from a plurality of known valid tests for components corresponding to the component 12 being evaluated, and averaging vibration output data from the plurality of tests to form the reference spectrum 32.

The criteria for comparing the test spectrum 30 to the reference spectrum 32 may comprise, for example, comparing a plurality of peak locations of the test spectrum 30 to particular preselected peak locations of the reference spectrum 32. The peak locations on the test spectrum 30 and reference spectrum 32 correspond to the frequencies of harmonic responses of the component 12 to the ultrasonic input frequency (20 kHz) of the transducer 14. For purposes of illustrating the present example, selected peak locations are identified as points A-F on the test and reference spectrums 30, 32 illustrated in FIGS. 2 and 3. It can be seen that the frequency of points A-F on the test spectrum 30 are the same as the frequency of corresponding points A-F on the reference spectrum 32, such that the test spectrum 30 may be identified as corresponding to a valid test, i.e., having a valid thermal imaging output. It should be understood that a greater or fewer number of points, or different points, may be selected for comparison of the test spectrum 30 to the reference spectrum 32. Further, it should be understood that a test is considered valid if it is determined that the input energy is sufficient to produce a thermal emission for identifying a defect in the component 12 and if the input energy is consistent with the input energy of other tests, as determined with reference to the reference spectrum 32.

Figure 4:
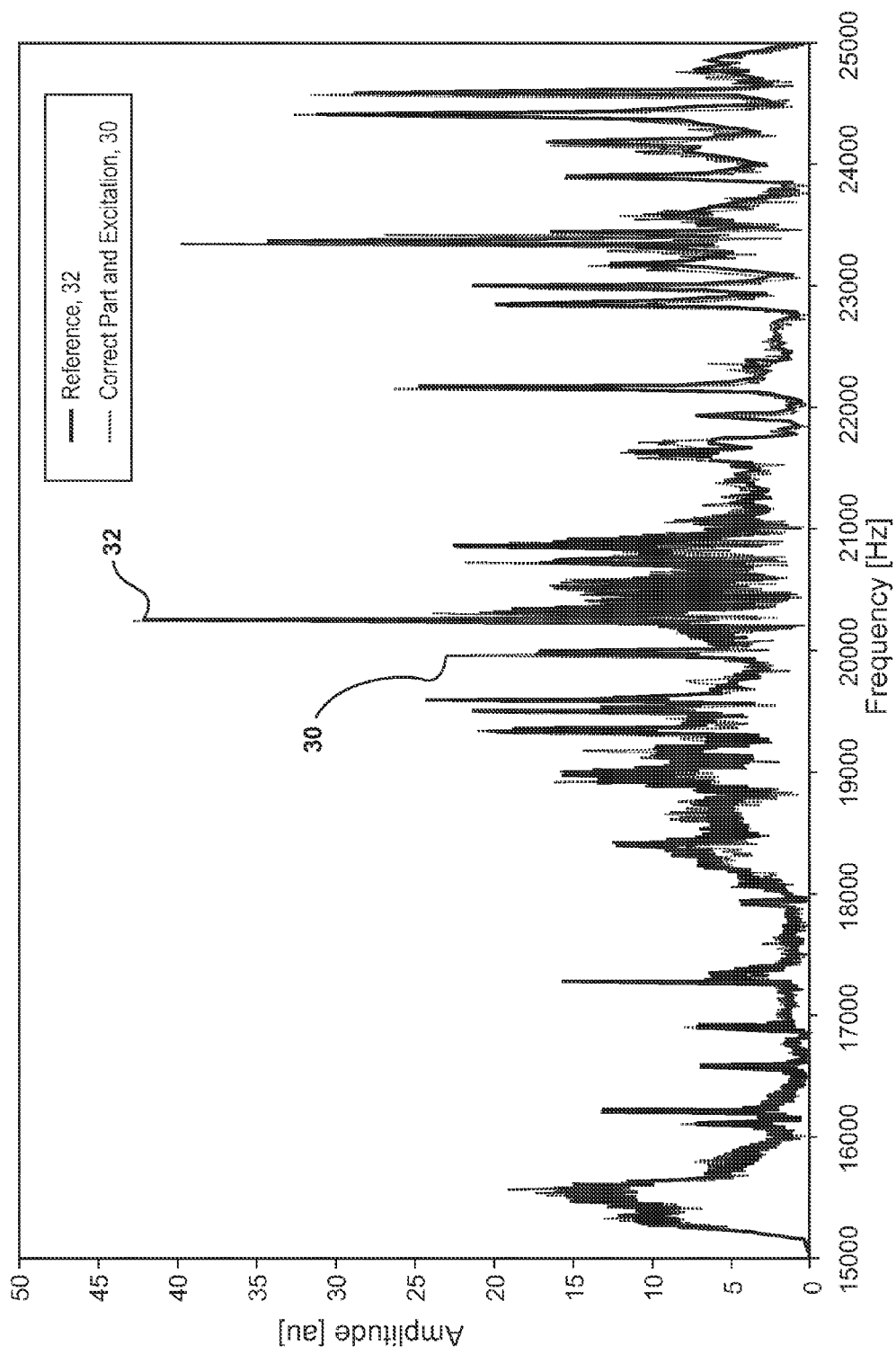
FIG. 4 shows the test spectrum of FIG. 2 overlaid on the reference spectrum of FIG. 3.

As seen in FIG. 4, in which the test spectrum 30 is overlaid on the reference spectrum 32, the frequency of substantially all of the peaks of the test spectrum 30 may match the frequency of the peaks of the reference spectrum 32. An accurate comparison of a test spectrum 30 to the reference spectrum 32 to filter test output signals 23 may be based on either substantially all or a selected number of the peak locations of the reference spectrum 32, wherein the required processing time may be reduced by selectively comparing less than all of the peak locations.

As an alternative or additional comparison, the amplitude of the harmonic frequency responses may be compared. The amplitudes illustrated herein are provided in arbitrary units (au). The amplitude comparison may be performed at selected frequencies of the reference spectrum 32, such as at the selected peak locations (frequencies) A-F, or any other selected peak locations. A predetermined amplitude value may be defined for each one of a selected peak location A-F, where the peaks in the test spectrum 30 must have an amplitude that substantially matches the selected amplitude values at the respective selected peak locations in order for the test output signal 23 to be considered valid.

Other methods of comparing the test spectrum 30 to the reference spectrum 32 may be implemented. For example, a correlation function may be applied to obtain a correlation score indicative of the similarity between the test spectrum 30 and the reference spectrum 32. The thermal imaging output may be identified for inclusion in an analysis of the component 12 if the correlation score of the correlation function is equal to or greater than a predetermined threshold value, and the thermal imaging output is filtered out of the analysis if the correlation score is below the threshold value.

Figure 5:
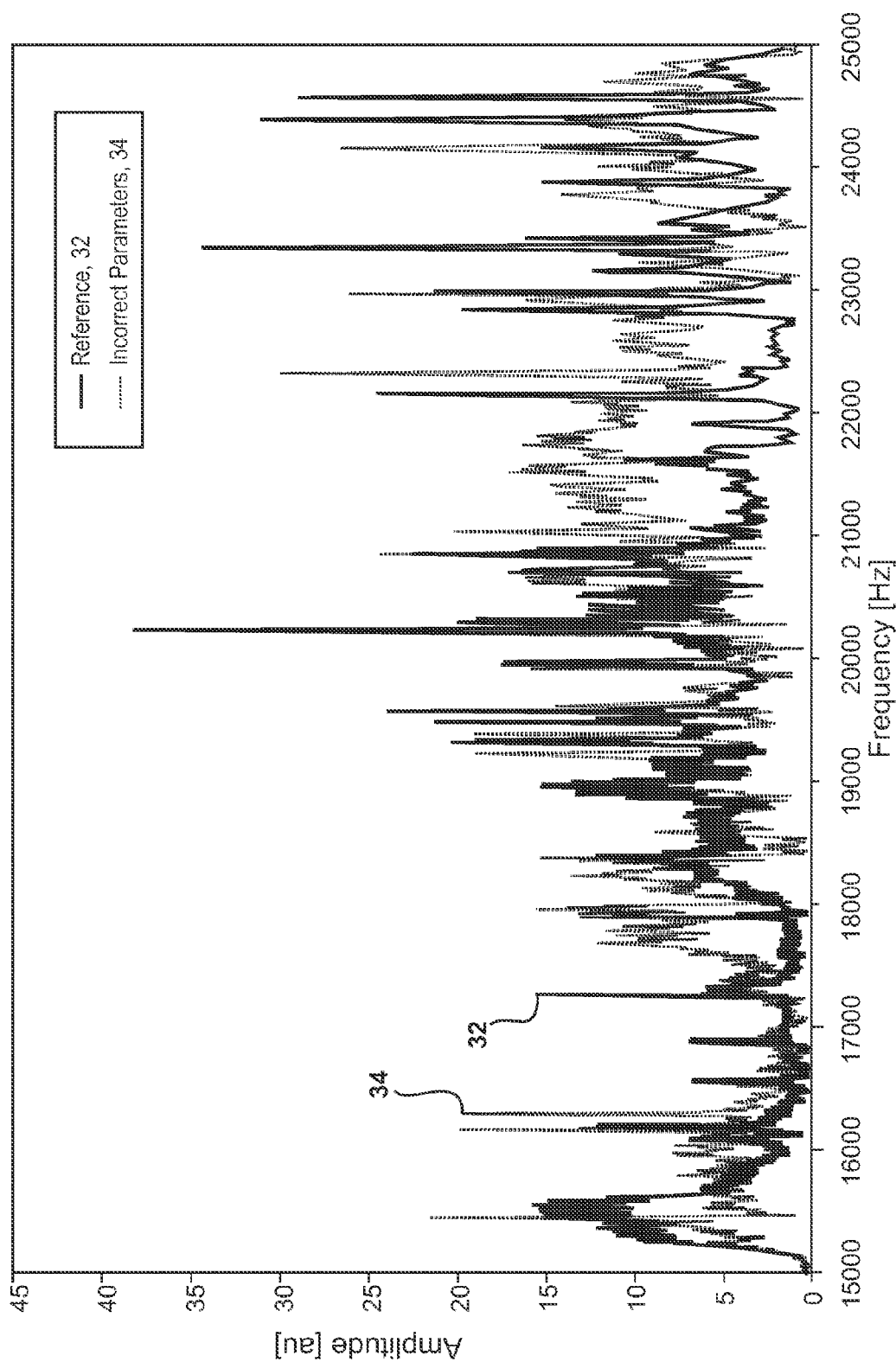
FIG. 5 shows a test spectrum in comparison to the reference spectrum wherein one or more of the parameters for providing input energy to the component are incorrect.
Figure 6:
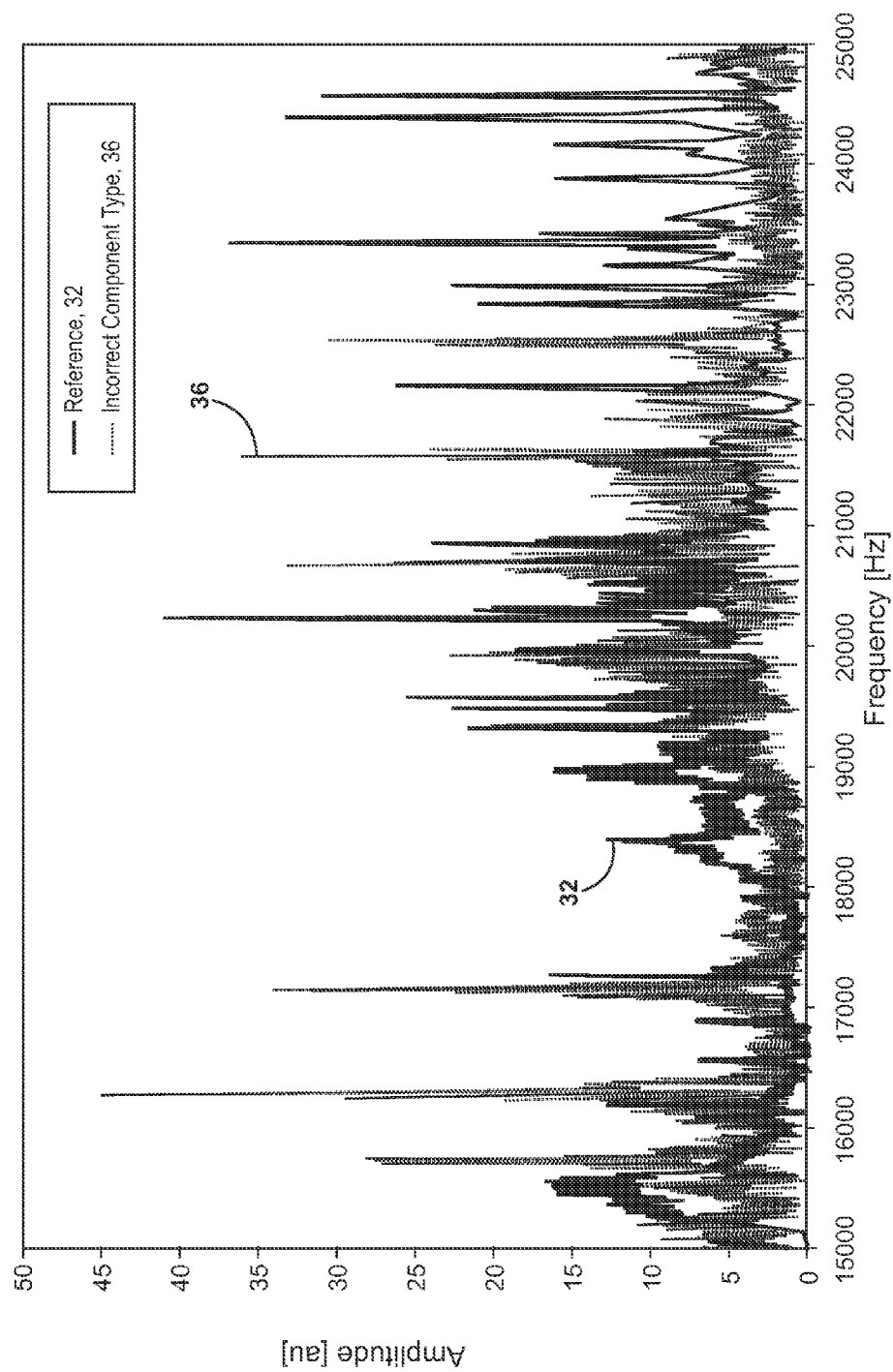
FIG. 6 shows a test spectrum in comparison to the reference spectrum wherein the component being tested comprises an incorrect component type.

FIGS. 5 and 6 illustrate examples of component tests where the thermal imaging output would be filtered out from results to be included in a component analysis. FIG. 5 shows a test spectrum 34 in comparison to the reference spectrum 32 wherein one or more of the parameters for providing input (excitation) energy to the component 12 are incorrect. For example, the test spectrum 34 may result from an incorrect frequency and or amplitude of the sound input signal, or from an improper force or coupling at the interface between the transducer 14 and the component 12. Additionally, the test spectrum 34 may be associated with a fault in the system 10 such as, for example, a broken piezo in the transducer 14. In the illustrated example, the test spectrum 34 includes peaks at locations (frequencies) other than the locations of the peaks of the reference spectrum 32, and the amplitude of peaks in the test spectrum 34 that coincide with peaks in the reference spectrum 32 generally have a substantially different amplitude than the reference spectrum 32.

FIG. 6 shows a test spectrum 36 in comparison to the reference spectrum 32 wherein the component 12 comprises an incorrect component type. For example, if the component 12 is a turbine blade, an incorrect component type may comprise a physical characteristic of the turbine blade, such as the weight or a dimensional characteristic (e.g., height, platform dimension, chord, etc.) of the turbine blade being different than the corresponding characteristic of the turbine blade used to form the reference spectrum 32. It can be seen that the vibration output of the incorrect component type, illustrated by the spectrum 36, has a substantially different frequency response in both peak location and amplitude. Hence, the thermal imaging output associated with the test spectrum 36 would be filtered out from the component analysis as not corresponding to the intended component type.

Figure 7:
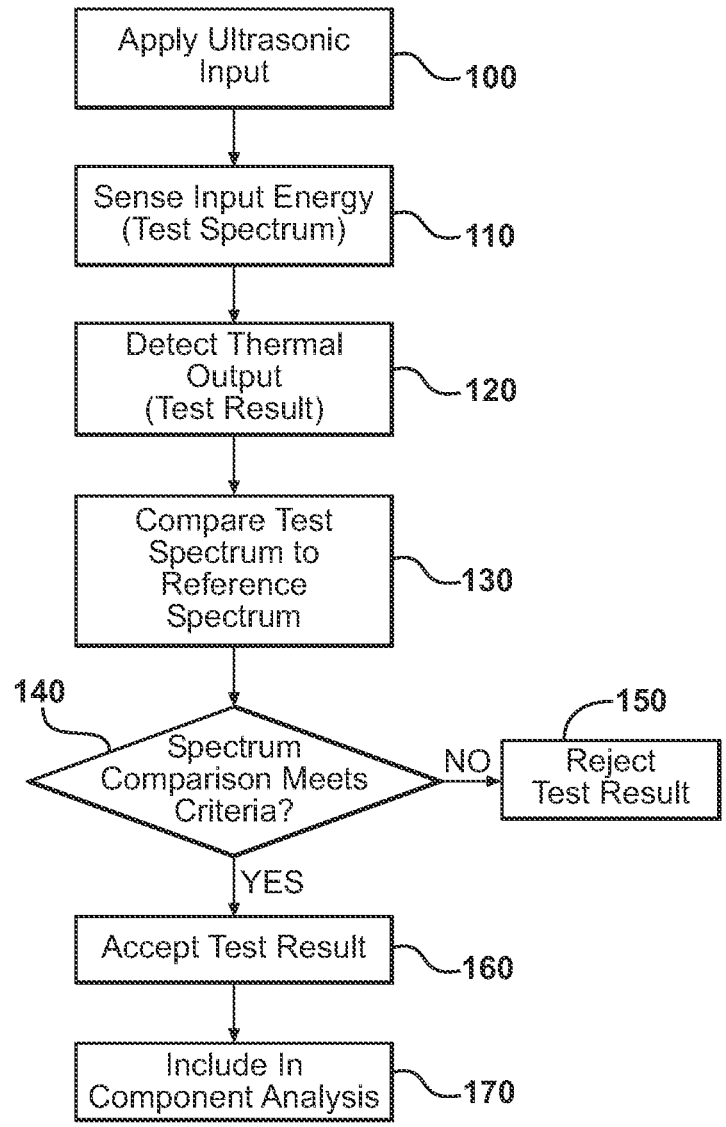
FIG. 7 is a flow diagram of the steps of a method for filtering out invalid test outputs from a component analysis.

FIG. 7 summarizes the steps of the method described above for filtering out invalid data from data used to detect defects in the component 12, which filtering may be performed by the processor 25. In particular, as seen in FIG. 7, the component analysis comprises the steps of: applying an ultrasonic sound input signal to the component 12, at 100; sensing an input energy corresponding to the sound input signal to the component 12, and producing a test spectrum, i.e., via a Fourier transform, at 110; detecting a thermal release or output from the component 12 and producing an output signal that may indicate a defect in the component, at 120; comparing the test spectrum to a reference (predetermined) spectrum, at 130; determining whether the result of the spectrum comparison meets a predetermined criteria, at step 140; and filtering the test result where the test result is rejected (step 150) if the comparison of step 140 does not meet the criteria, and the test result is accepted (step 160) if the comparison of step 140 does meet the criteria. Subsequently, the accepted test result is provided to a component analysis (step 170) for evaluating the component 12 for structural defects.

From the above it should be understood that the initial quantitative determination of the test process provides an evaluation of the input acoustic energy to ensure that sufficient energy is input to the component 12 for the inspection process, and to provide a consistent energy input from component to component and over time, i.e., from day to day. That is, the test process described herein facilitates identification of variable conditions in non-destructive testing of components 12, providing consistency in the testing between multiple components 12, and in evaluating the same component 12 over the life the component 12. Further, the present test process provides a quantitative analysis of the input excitation energy for an acoustic thermography test which may be implemented through an automated process performed by a processor such as a microcontroller or in a computer.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of performing acoustic thermography on a structure, the method comprising:
   applying a sound input signal to the structure;
   sensing an input energy corresponding to the sound input signal applied to the structure, and the sensing an input energy comprising producing an input energy signal corresponding to the sensed input energy;
   detecting a thermal release from the structure produced as a result of the sound input signal and producing an output signal effective to indicate a defect in the structure;
   verifying an input power of the sound input signal to the structure based on a comparison of the input energy signal to a reference signal; and
   performing a filtering of the output signal including identifying the output signal for inclusion in an analysis based on a comparison of the input energy signal to the reference signal;
   wherein the step of comparing the input energy signal to the reference signal includes:
   a) applying a Fourier transform to the input energy signal to provide a test Fourier transform spectrum of the vibration output, and the reference signal comprises a predetermined reference Fourier transform spectrum for comparison to the test Fourier transform spectrum of the vibration output;
   b) determining whether a criteria is met comprising identifying a correspondence of peak locations between the test and reference Fourier transform spectra, indicating a predetermined level of correspondence of harmonic response frequencies between the input energy signal and the reference signal; and
   c) determining whether at least one other criteria is met, the at least one other criteria characterizing an input energy of the test Fourier transform relative to the reference Fourier transform at the harmonic response frequencies.

2. The method of claim 1, wherein the sensing an input energy comprises receiving a vibration output from the structure at a sensor producing the input energy signal.

3. The method of claim 1, wherein the test Fourier transform spectrum of the vibration output and the predetermined reference Fourier transform spectrum each comprises peaks corresponding to harmonic response frequencies and the filtering comprises identifying the output signal for inclusion in an analysis of the structure if the frequencies of a predetermined number of peaks in the test Fourier transform spectrum of the vibration output occur at the same frequencies as the peaks in the predetermined reference Fourier transform spectrum.

4. The method of claim 1, wherein the test Fourier transform spectrum of the vibration output and the predetermined reference Fourier transform spectrum each comprises peaks corresponding to harmonic response frequencies and the filtering comprises identifying the output signal for inclusion in an analysis of the structure if the amplitude of the peaks in the test Fourier transform spectrum of the vibration output substantially matches the amplitude of the peaks in the predetermined reference Fourier transform spectrum at predetermined corresponding frequencies.

5. The method of claim 1, wherein the filtering comprises implementing a correlation function to compare the test Fourier transform spectrum of the vibration output to the predetermined reference Fourier transform spectrum and identifying the output signal for inclusion in an analysis of the structure if a correlation score of the correlation function is equal to or greater than a predetermined threshold value.

6. The method of claim 1, wherein the sensing an input energy comprises detecting an emitted sound signal emitted from the structure, and the emitted sound signal is received by a microphone spaced from the structure and producing the input energy signal.

7. The method of claim 1, wherein the sound input signal comprises an ultrasonic sound input signal.

8. The method of claim 1, wherein the detecting a thermal release comprises receiving the thermal release at an infrared camera and producing the output signal.

9. A method of performing acoustic thermography on a structure, the method comprising:
applying an ultrasonic sound input signal to the structure;
sensing an input energy corresponding to the sound input signal applied to the structure, and the sensing an input energy comprising receiving a vibration output from the structure at a sensor producing an input energy signal corresponding to the sensed input energy;
applying a Fourier transform to the input energy signal to provide a test Fourier transform spectrum of the vibration output;
detecting a thermal release from the structure produced as a result of the sound input signal and producing an output signal effective to indicate a defect in the structure;
verifying an input power of the sound input signal to the structure based on a comparison of the test Fourier transform spectrum of the vibration output to a predetermined reference Fourier transform spectrum; and
performing a filtering of the output signal including identifying the output signal for inclusion in an analysis of the structure if the input power of the sound input signal meets a predetermined criteria based on the comparison of the test Fourier transform spectrum of the vibration output to the predetermined reference Fourier transform spectrum;
wherein the step of comparing the test Fourier transform spectrum to the reference Fourier transform spectrum includes:
a) determining whether a criteria is met comprising identifying a correspondence of peak locations between the test and reference Fourier transform spectra, indicating a predetermined level of correspondence of harmonic response frequencies between the input energy signal and the reference signal; and
b) determining whether at least one other criteria is met, the at least one other criteria characterizing an input energy of the test Fourier transform relative to the reference Fourier transform at the harmonic response frequencies.

10. The method of claim 9, wherein the test Fourier transform spectrum of the vibration output and the predetermined reference Fourier transform spectrum each comprises peaks corresponding to harmonic response frequencies and the filtering comprises identifying the output signal for inclusion in an analysis of the structure if the frequencies of a predetermined number of peaks in the test Fourier transform spectrum of the vibration output occur at the same frequencies as the peaks in the predetermined reference Fourier transform spectrum.

11. The method of claim 9, wherein the test Fourier transform spectrum of the vibration output and the predetermined reference Fourier transform spectrum each comprises peaks corresponding to harmonic response frequencies and the filtering comprises identifying the output signal for inclusion in an analysis of the structure if the amplitude of the peaks in the test Fourier transform spectrum of the vibration output substantially matches the amplitude of the peaks in the predetermined reference Fourier transform spectrum at predetermined corresponding frequencies.

12. The method of claim 9, wherein the filtering comprises implementing a correlation function to compare the test Fourier transform spectrum of the vibration output to the predetermined reference Fourier transform spectrum and identifying the output signal for inclusion in an analysis of the structure if a correlation score of the correlation function is equal to or greater than a predetermined threshold value.

13. The method of claim 9, wherein the sensing an input energy comprises detecting an emitted sound signal emitted from the structure, and the emitted sound signal is received by a microphone spaced from the structure and producing the input energy signal.

14. The method of claim 9, the filtering including using the comparison of the test Fourier transform spectrum of the vibration output to a predetermined reference Fourier transform spectrum to determine that at least one parameter affecting application of the ultrasonic sound input signal to the structure is incorrect.

15. The method of claim 9, wherein the predetermined reference Fourier transform spectrum corresponds to a predetermined structure, and the filtering including using the comparison of the test Fourier transform spectrum of the vibration output to a predetermined reference Fourier transform spectrum to determine that the structure to which the ultrasonic sound signal is applied is different from the predetermined structure corresponding to the predetermined reference Fourier transform spectrum.

16. A system for performing acoustic thermography on a structure, the system comprising:
an acoustic energy source for applying a sound input signal to the structure;
a sensor for sensing an input energy corresponding to the acoustic input energy signal corresponding to the sensed input energy;
an infrared camera configured to detect a thermal energy release from the structure produced as a result of the sound input and producing an output signal indicative of a defect in the structure; and a processor configured for receiving the input energy and the output signal, the processor configured for processing the input energy signal and verifying an input power of the sound input signal to the structure based on a comparison of the input energy signal to a reference signal, and the processor configured for performing a filtering of the output signal including identifying whether to include the output signal in an analysis of the structure based on the comparison of the input energy signal to the reference signal;

wherein the processor is configured to compare the input energy signal to the reference signal by:

a) applying a Fourier transform to the input energy signal to provide a test Fourier transform spectrum of the vibration output, and the reference signal comprises a predetermined reference Fourier transform spectrum for comparison to the test Fourier transform spectrum of the vibration output;

b) determining whether a criteria is met comprising identifying a correspondence of peak locations between the test and reference Fourier transform spectra, indicating a predetermined level of correspondence of harmonic response frequencies between the input energy and the reference signal; and c) determining whether the at least one other criteria is met, the at least one other criteria characterizing an input energy of the test Fourier transform relative to the reference Fourier transform at the harmonic response frequencies.

17. The system of claim 16, wherein the sensor for sensing input energy is located spaced from the acoustic energy source and the structure.

18. The system of claim 17, wherein the sensor for sensing the input energy and producing the input energy signal comprises a microphone.

19. The system of claim 16, wherein the acoustic energy source comprises an ultrasonic transducer coupled to the structure whereby ultrasonic energy is transmitted from the ultrasonic transducer to the structure.

* * * * *